United States Patent
Sasikumar et al.

(10) Patent No.: US 9,776,978 B2
(45) Date of Patent: Oct. 3, 2017

(54) 1,3,4-OXADIAZOLE AND 1,3,4-THIADIAZOLE DERIVATIVES AS IMMUNOMODULATORS

(71) Applicants: Pottayil Govindan Nair Sasikumar, Bangalore (IN); Muralidhara Ramachandra, Bangalore (IN); Seetharamaiah Setty Sudarshan Naremaddepalli, Bangalore (IN)

(72) Inventors: Pottayil Govindan Nair Sasikumar, Bangalore (IN); Muralidhara Ramachandra, Bangalore (IN); Seetharamaiah Setty Sudarshan Naremaddepalli, Bangalore (IN)

(73) Assignee: Aurigene Discovery Technologies Limited, Bangalore (IN)

( * ) Notice: Subject to any disclaimer, the term of this patent is extended or adjusted under 35 U.S.C. 154(b) by 0 days.

(21) Appl. No.: 15/296,292

(22) Filed: Oct. 18, 2016

(65) Prior Publication Data

US 2017/0101387 A1 Apr. 13, 2017

Related U.S. Application Data

(63) Continuation of application No. 14/916,290, filed as application No. PCT/IB2014/064281 on Sep. 5, 2014, now abandoned.

(30) Foreign Application Priority Data

Sep. 6, 2013 (IN) ............................ 4012/CHE/2013

(51) Int. Cl.
| | |
|---|---|
| *C07D 285/12* | (2006.01) |
| *C07D 271/10* | (2006.01) |
| *A61K 31/433* | (2006.01) |
| *A61K 45/06* | (2006.01) |
| *A61K 31/4245* | (2006.01) |

(52) U.S. Cl.
CPC ........ *C07D 285/12* (2013.01); *A61K 31/4245* (2013.01); *A61K 31/433* (2013.01); *A61K 45/06* (2013.01); *C07D 271/10* (2013.01)

(58) Field of Classification Search
None
See application file for complete search history.

(56) References Cited

U.S. PATENT DOCUMENTS

| | | |
|---|---|---|
| 8,735,553 B1 | 5/2014 | Li et al. |
| 2012/0232268 A1* | 9/2012 | Burgess ............... C07D 241/08 544/198 |

FOREIGN PATENT DOCUMENTS

| | | |
|---|---|---|
| WO | 0114557 A1 | 3/2001 |
| WO | 02079499 A1 | 10/2002 |
| WO | 02086083 A2 | 10/2002 |
| WO | 03042402 A2 | 5/2003 |
| WO | 2004004771 A1 | 1/2004 |
| WO | 2004056875 A1 | 7/2004 |
| WO | 2006121168 A1 | 11/2006 |
| WO | 2008156712 A1 | 12/2008 |
| WO | 2010077634 A1 | 7/2010 |
| WO | 2011066389 A1 | 6/2011 |
| WO | 2011161699 A2 | 12/2011 |
| WO | 2012168944 A1 | 12/2012 |
| WO | 2013132317 A1 | 9/2013 |
| WO | 2013144704 A1 | 10/2013 |
| WO | 2014055897 A2 | 4/2014 |
| WO | 2014059173 A2 | 4/2014 |
| WO | 2014100079 A1 | 6/2014 |

OTHER PUBLICATIONS

Ko et al., Journal of the American Chemical Society (2011), 133(3), pp. 462-477.*
Harvey RD. Immunologic and Clinical Effects of Targeting PD-1 in Lung Cancer, Clinical Pharmacology & Therapeutics (2014) 96 (02) : 214-223.
Pedoeem, et al. Programmed death-1 pathway in cancer and autoimmunity, Clinical Immunology (2014) 153:145-152.
Shi et al. The role of PD-1 and PD-L1 in T-cell immune suppression in patients with hematological malignancies. Journal of Hematology & Oncology 2013, 6:74 p. 1-6.
Jin et al. Role of PD-1 in Regulating T-Cell Immunity. Current Topics in Microbiology and Immunology (2010) published online: Sep. 11, 2010 350: pp. 17-37.

* cited by examiner

*Primary Examiner* — Brian J Davis
(74) *Attorney, Agent, or Firm* — Benjamin Aaron Adler

(57) ABSTRACT

The present invention relates to 1,3,4-oxadiazole and 1,3,4-thiadiazole compounds as therapeutic agents capable of inhibiting the programmed cell death 1 (PD1) signalling pathway. The invention also refers to derivatives of the therapeutic agents. The invention also encompasses the use of the said therapeutic agents and derivatives for treatment of disorders via immunopotentiation comprising inhibition of immunosuppressive signal induced due to PD-1, PD-L1, or PD-L2 and therapies using them.

55 Claims, No Drawings

1,3,4-OXADIAZOLE AND 1,3,4-THIADIAZOLE DERIVATIVES AS IMMUNOMODULATORS

CROSS-REFERENCE TO RELATED APPLICATIONS

This application is a continuation of pending U.S. Ser. No. 14/916,290, filed Mar. 3, 2016, which is a national stage application under 35 U.S.C.§371 of international application PCT/IB2014/064281, filed on Sep. 5, 2014, now abandoned, which claims the benefit of priority to Indian provisional application number 4012/CHE/2013, filed Sep. 6, 2013, now abandoned, the contents of all of which are hereby incorporated by reference in their entireties.

BACKGROUND OF THE INVENTION

Technical Field

The present invention relates to 1,3,4-oxadiazole and 1,3,4-thiadiazole compounds therapeutically useful as immune modulators. The invention also relates to pharmaceutical compositions comprising the said 1,3,4-oxadiazole and 1,3,4-thiadiazole compounds as therapeutic agents.

Description of the Related Art

Programmed cell death-1 (PD-1) is a member of the CD28 superfamily that delivers negative signals upon interaction with its two ligands, PD-L1 or PD-L2. PD-1 and its ligands are broadly expressed and exert a wider range of immunoregulatory roles in T cells activation and tolerance compared with other CD28 members. PD-1 and its ligands are involved in attenuating infectious immunity and tumor immunity, and facilitating chronic infection and tumor progression. The biological significance of PD-1 and its ligand suggests the therapeutic potential of manipulation of PD-1 pathway against various human diseases (Ariel Pedoeem et al., Curr Top Microbiol Immunol. (2011); 350:17-37).

T-cell activation and dysfunction relies on direct and modulated receptors. Based on their functional outcome, co-signaling molecules can be divided as co-stimulators and co-inhibitors, which positively and negatively control the priming, growth, differentiation and functional maturation of a T-cell response (Li Shi, et al., Journal of Hematology & Oncology 2013, 6:74).

Therapeutic antibodies that block the programmed cell death protein-1 (PD-1) immune checkpoint pathway prevent T-cell down regulation and promote immune responses against cancer. Several PD-1 pathway inhibitors have shown robust activity in various phases of clinical trials (R D Harvey, Clinical Pharmacology & Therapeutics (2014); 96 2, 214-223).

Programmed death-1 (PD-1) is a co-receptor that is expressed predominantly by T cells. The binding of PD-1 to its ligands, PD-L1 or PD-L2, is vital for the physiological regulation of the immune system. A major functional role of the PD-1 signaling pathway is the inhibition of self-reactive T cells, which serve to protect against autoimmune diseases. Elimination of the PD-1 pathway can therefore result in the breakdown of immune tolerance that can ultimately lead to the development of pathogenic autoimmunity. Conversely, tumor cells can at times co-opt the PD-1 pathway to escape from immunosurveillance mechanisms. Therefore, blockade of the PD-1 pathway has become an attractive target in cancer therapy. Current approaches include six agents that are either PD-1 and PD-L1 targeted neutralizing antibodies or fusion proteins. More than forty clinical trials are underway to better define the role of PD-1 blockade in variety of tumor types. (Hyun-Tak Jin et al., Clinical Immunology (Amsterdam, Netherlands) (2014), 153(1), 145-152).

International applications WO 01/14557, WO 02/079499, WO 2002/086083, WO 03/042402, WO 2004/004771, WO 2004/056875, WO2006121168, WO2008156712, WO2010077634, WO2011066389, WO2014055897, WO2014059173, WO2014100079 and U.S. patent U.S. Ser. No. 08/735,553 report PD-1 or PD-L1 inhibitory antibodies or fusion proteins.

Further, International applications, WO2011161699, WO2012/168944, WO2013144704 and WO2013132317 report peptides or peptidomimetic compounds which are capable of suppressing and/or inhibiting the programmed cell death 1 (PD1) signaling pathway.

Still there is a need for more potent, better and/or selective immune modulators of PD-1 pathway. The present invention provides 1,3,4-oxadiazole and 1,3,4-thiadiazole compounds which are capable of suppressing and/or inhibiting the programmed cell death 1 (PD1) signalling pathway.

SUMMARY OF INVENTION

In accordance with the present invention, 1,3,4-oxadiazole and 1,3,4-thiadiazole compounds or a pharmaceutically acceptable salt or a stereoisomer thereof, provided which are capable of suppressing and/or inhibiting the programmed cell death 1 (PD1) signalling pathway.

In one aspect, the present invention provides a 1,3,4-oxadiazole and 1,3,4-thiadiazole compounds of formula (I):

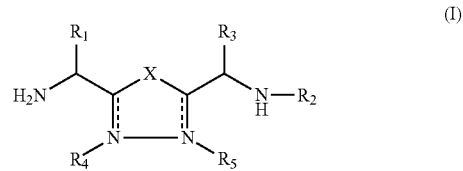

(I)

wherein,
R$_1$ is side chain of an amino acid selected from Ser, Thr, Phe, Ala or Asn;
X is S or O;
R$_2$ is hydrogen or —CO-Aaa;
Aaa is an amino acid residue selected from Ser, Asn or Thr; wherein a C-terminus thereof is a free terminus, is amidated or is esterified;
R$_3$ is side chain of an amino acid selected from Ser, Ala, Glu, Gln, Asn or Asp;
— is an optional bond;
R$_4$ and R$_5$ independently are hydrogen or absent;
or a pharmaceutically acceptable salt or a stereoisomer thereof.

In a further aspect of the present invention, it relates to the pharmaceutical composition comprising a compound of formula (I) or a pharmaceutically acceptable salt or a stereoisomer and processes for preparing thereof.

In yet another aspect of the present invention, it provides use of 1,3,4-oxadiazole and 1,3,4-thiadiazole compounds of formula (I) or a pharmaceutically acceptable salt or a stereoisomer thereof, which are capable of suppressing and/or inhibiting the programmed cell death 1 (PD1) signaling pathway.

DETAILED DESCRIPTION OF THE INVENTION

The present invention provides 1,3,4-oxadiazole and 1,3,4-thiadiazole compounds as therapeutic agents useful for treatment of disorders via immunopotentiation comprising inhibition of immunosuppressive signal induced due to PD-1, PD-L1, or PD-L2 and therapies using them.

Each embodiment is provided by way of explanation of the invention, and not by way of limitation of the invention. In fact, it will be apparent to those skilled in the art that various modification and variations can be made in the present invention without departing from the scope or spirit of the invention. For instance, features illustrated or described as part of one embodiment can be used on another embodiment to yield a still further embodiment. Thus it is intended that the present invention cover such modifications and variations as come within the scope of the appended claims and their equivalents. Other objects, features, and aspects of the present invention are disclosed in, or are obvious from, the following detailed description. It is to be understood by one of ordinary skill in the art that the present discussion is a description of exemplary embodiments only, and is not to be construed as limiting the broader aspects of the present invention.

In one embodiment, the present invention relates to compounds of formula (I)

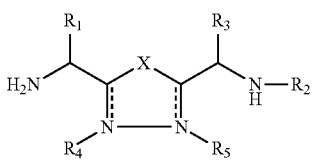

(I)

wherein,
$R_1$ is side chain of an amino acid selected from Ser, Thr, Phe, Ala or Asn;
X is S or O;
$R_2$ is hydrogen or —CO-Aaa;
Aaa is an amino acid residue selected from Ser, Asn or Thr; wherein a C-terminus thereof is a free terminus, is amidated or is esterified;
$R_3$ is side chain of an amino acid selected from Ser, Ala, Glu, Gln, Asn or Asp;
— is an optional bond;
$R_4$ and $R_5$ independently are hydrogen or absent;
or a pharmaceutically acceptable salt or a stereoisomer thereof.

In yet another embodiment, the present invention provides compounds of formula (IA)

(IA)

or a pharmaceutically acceptable salt or a stereoisomer thereof; wherein,
$R_1$ is side chain of an amino acid selected from Ser, Thr, Phe, Ala or Asn;
X is S or O;
$R_2$ is hydrogen or —CO-Aaa;
$R_3$ is side chain of an amino acid selected from Ser, Ala, Glu, Gln, Asn or Asp;
Aaa is an amino acid residue selected from Ser, Asn or Thr; wherein a C-terminus thereof is a free terminus, is amidated or is esterified.

In yet another further embodiment, the present invention provides compounds of formula (IB)

(IB)

or a pharmaceutically acceptable salt or a stereoisomer thereof; wherein,
$R_1$ is side chain of an amino acid selected from Ser, Thr, Phe, Ala or Asn;
$R_3$ is side chain of an amino acid selected from Ser, Ala, Glu, Gln, Asn or Asp;
Aaa is an amino acid residue selected from Ser, Asn or Thr; wherein a C-terminus thereof is a free terminus, is amidated or is esterified.

In yet another further embodiment, the present invention provides compounds of formula (IC)

(IC)

or a pharmaceutically acceptable salt or a stereoisomer thereof; wherein,
$R_1$ is side chain of an amino acid selected from Ser, Thr, Phe, Ala or Asn;
$R_3$ is side chain of an amino acid selected from Ser, Ala, Glu, Gln, Asn or Asp;
Aaa is an amino acid residue selected from Ser, Asn or Thr; wherein a C-terminus thereof is a free terminus, is amidated or is esterified.

In yet another further embodiment, the present invention provides compounds of formula (I), wherein,
$R_1$ is side chain of Ser or Thr;
$R_2$ is —CO-Aaa;
Aaa is an amino acid residue Ser or Thr; wherein the C-terminus is free;
$R_3$ is side chain of Asn, Gln, Glu or Asp.

The embodiment below are illustrative of the present invention and are not intended to limit the claims to the specific embodiments exemplified.

According to one embodiment, specifically provided are compounds of the formula (I) and (IA), in which X is O.

According to another embodiment, specifically provided are compounds of the formula (I) and (IA) in which X is S.

According to yet another embodiment, specifically provided are compounds of the formula (I) and (IA) in which $R_2$ is hydrogen.

According to yet another embodiment, specifically provided are compounds of the formula (I) in which $R_4$ and $R_5$ are hydrogen.

According to yet another embodiment, specifically provided are compounds of the formula (I) in which $R_4$ and $R_5$ are absent.

According to yet another embodiment, specifically provided are compounds of the formula (I) in which $R_2$ is —CO-Ser.

According to yet another embodiment, specifically provided are compounds of the formula (I) in which $R_2$ is —CO-Thr.

According to yet another embodiment, specifically provided are compounds of the formula (I), (IA), (IB) and (IC) in which $R_1$ is side chain of Ser.

According to yet another embodiment, specifically provided are compounds of the formula (I), (IA), (IB) and (IC) in which $R_1$ is side chain of Thr.

According to yet another embodiment, specifically provided are compounds of the formula (I), (IA) and (IC) in which $R_1$ is side chain of Phe, Ala or Asn.

According to yet another embodiment, specifically provided are compounds of the formula (I), (IA), (IB) and (IC) in which $R_3$ is side chain of Asn.

According to yet another embodiment, specifically provided are compounds of the formula (I), (IA) and (IB) in which $R_3$ is side chain of Ser.

According to yet another embodiment, specifically provided are compounds of the formula (I), (IA) and (IC) in which $R_3$ is side chain of Gln.

According to yet another embodiment, specifically provided are compounds of the formula (I), (IA) and (IC) in which $R_3$ is side chain of Glu.

According to yet another embodiment, specifically provided are compounds of the formula (I), (IA) and (IC) in which $R_3$ is side chain of Ala or Asp.

According to yet another embodiment, specifically provided are compounds of the formula (IB) and (IC) in which Aaa is Ser.

According to yet another embodiment, specifically provided are compounds of the formula (IC) in which Aaa is Thr.

According to yet another embodiment, specifically provided are compounds of the formula (I), (IA) and (IB) in which one, more or all amino acid/s is/are D amino acid/s.

In an embodiment, specific compounds of formula (I) without any limitation are enumerated in Table (1).

TABLE 1

| Compound No. | Structure |
|---|---|
| 1. | [structure] |
| 2. | [structure] |
| 3. | [structure] |
| 4. | [structure] |
| 5. | [structure] |
| 6. | [structure] |
| 7. | [structure] |
| 8. | [structure] |
| 9. | [structure] |
| 10. | [structure] |

TABLE 1-continued

| Compound No. | Structure |
|---|---|
| 11. | [structure] |
| 12. | [structure] |
| 13. | [structure] |
| 14. | [structure] |
| 15. | [structure] |
| 16. | [structure] |
| 17. | [structure] |
| 18. | [structure] and |
| 19. | [structure] |
| 20. | [structure] | or a pharmaceutically acceptable salt thereof or a stereoisomer thereof.

The compounds as disclosed in the present invention are formulated for pharmaceutical administration.

In one embodiment, the present invention provides a pharmaceutical composition comprising the compound as disclosed, and a pharmaceutically acceptable carrier or a diluent.

In another embodiment, the said pharmaceutical composition further comprising at least one of an anticancer agent, chemotherapy agent, or antiproliferative compound.

In one embodiment, the present invention provides the compounds as disclosed in the present invention for use as a medicament.

In another embodiment, the present invention provides the compounds as disclosed in the present invention for use as a medicament for the treatment of cancer or infectious disease.

In another embodiment, the present invention provides the compounds as disclosed in the present invention for use as a medicament for the treatment bone cancer, cancer of the head or neck, pancreatic cancer, skin cancer, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumours of childhood, lymphocytic lymphoma, cancer of the bladder, cancer of the kidney or ureter, carcinoma of the renal pelvis, neoplasm of the central nervous system (CNS), primary CNS lymphoma, tumour angiogenesis, spinal axis tumour, brain stem glioma, pituitary adenoma, Kaposi's sarcoma, epidermoid cancer, squamous cell cancer, T-cell lymphoma, environmentally induced cancers including those induced by asbestos, and combinations of said cancers.

In another embodiment, the present invention provides the compounds as disclosed in the present invention for use in the treatment of cancer.

In another embodiment, the present invention provides the compounds as disclosed in the present invention for use in the treatment of infectious disease.

In one embodiment, the present invention provides the compounds as disclosed in the present invention for use as a medicament for the treatment of bacterial infectious disease, a viral infectious disease or a fungal infectious disease.

In one embodiment, the present invention provides a method of treatment of cancer, wherein the method comprises administration of an effective amount of the compound of the present invention to the subject in need thereof.

In another embodiment the present invention provides a method of modulating an immune response mediated by PD-1 signaling pathway in a subject, comprising administering to the subject therapeutically effective amount of the compound of the present invention such that the immune response in the subject is modulated.

In yet another embodiment the present invention provides a method of inhibiting growth of tumour cells and/or metastasis in a subject, comprising administering to the subject a therapeutically effective amount of compound of the present invention capable of inhibiting the programmed cell death 1 (PD1) signaling pathway.

The said tumour cells include cancer such as but not limited to bone cancer, cancer of the head or neck, pancreatic cancer, skin cancer, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumours of childhood, lymphocytic lymphoma, cancer of the bladder, cancer of the kidney or ureter, carcinoma of the renal pelvis, neoplasm of the central nervous system (CNS), primary CNS lymphoma, tumour angiogenesis, spinal axis tumour, brain stem glioma, pituitary adenoma, Kaposi's sarcoma, epidermoid cancer, squamous cell cancer, T-cell lymphoma, environmentally induced cancers including those induced by asbestos, and combinations of said cancers.

In yet another further embodiment the present invention provides a method of treating an infectious disease in a subject comprising administering to the subject a therapeutically effective amount of the compound of the present invention capable of inhibiting the programmed cell death 1 (PD1) signaling pathway such that the subject is treated for the infectious disease.

Still yet another embodiment of the present invention provides a method of treating bacterial, viral and fungal infections in a subject comprising administering to the subject a therapeutically effective amount of the compound of the present invention capable of inhibiting the programmed cell death 1 (PD1) signalling pathway such that the subject is treated for the bacterial, viral and fungal infections.

The infectious disease includes but not limited to HIV, Influenza, Herpes, Giardia, Malaria, *Leishmania*, the pathogenic infection by the virus Hepatitis (A, B, & C), herpes virus (e.g., VZV, HSV-I, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus, pathogenic infection by the bacteria *chlamydia*, rickettsial bacteria, mycobacteria, staphylococci, streptococci, pneumonococci, meningococci and conococci, *klebsiella, proteus, serratia, pseudomonas, E. coli, legionella*, diphtheria, *salmonella*, bacilli, cholera, tetanus, botulism, anthrax, plague, leptospirosis, and Lyme's disease bacteria, pathogenic infection by the fungi *Candida* (*albicans, krusei, glabrata, tropicalis*, etc.), *Cryptococcus neoformans, Aspergillus* (*fumigatus, niger*, etc.), Genus *Mucorales* (*mucor, absidia, rhizophus*), *Sporothrix schenkii, Blastomyces dermatitidis, Paracoccidioides brasiliensis, Coccidioides immitis* and *Histoplasma capsulatum*, and pathogenic infection by the parasites *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, Nippostrongylus brasiliensis.

The compounds of the present invention may be used as single drugs or as a pharmaceutical composition in which the compound is mixed with various pharmacologically acceptable materials.

The pharmaceutical composition is usually administered by oral or inhalation routes, but can be administered by parenteral administration route. In the practice of this invention, compositions can be administered, for example, by orally, intravenous infusion, topically, intraperitoneally, intravesically or intrathecally. Examples of the parenteral administration includes but not limited to intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Oral administration, parenteral administration, subcutaneous administration and intravenous administration are the preferred methods of administration.

The dosage of the compounds of the present invention varies depending on age, weight, symptom, therapeutic efficacy, dosing regimen and/or treatment time. Generally, they may be administered by oral or inhalation routes, in an amount of 1 mg to 100 mg per time, from once a couple of days, once 3 days, once 2 days, once a day to a couple of times a day, in the case of an adult, or continuously administered by oral or inhalation routes from 1 to 24 hours a day. Since the dosage is affected by various conditions, an amount less than the above dosage may sometimes work well enough, or higher dosage may be required in some cases.

The compounds of the present invention may be administered in combination with other drugs for (1) complementation and/or enhancement of prevention and/or therapeutic efficacy of the preventive and/or therapeutic drug of the present invention, (2) dynamics, absorption improvement, dosage reduction of the preventive and/or therapeutic drug of the present invention, and/or (3) reduction of the side effects of the preventive and/or therapeutic drug of the present invention.

A concomitant medicine comprising the compounds of the present invention and other drug may be administered as a combination preparation in which both components are contained in a single formulation, or administered as separate formulations. The administration by separate formulations includes simultaneous administration and administration with some time intervals. In the case of the administration with some time intervals, the compound of the present invention can be administered first, followed by another drug or another drug can be administered first, followed by the compound of the present invention. The administration method of the respective drugs may be the same or different.

The dosage of the other drug can be properly selected, based on a dosage that has been clinically used. The compounding ratio of the compound of the present invention and the other drug can be properly selected according to age and weight of a subject to be administered, administration method, administration time, disorder to be treated, symptom and combination thereof. For example, the other drug may be used in an amount of 0.01 to 100 parts by mass, based on 1 part by mass of the compound of the present invention. The other drug may be a combination of two or more kind of arbitrary drugs in a proper proportion. The other drug that complements and/or enhances the preventive and/or therapeutic efficacy of the compound of the present invention includes not only those that have already been discovered, but those that will be discovered in future, based on the above mechanism.

Diseases on which this concomitant use exerts a preventive and/or therapeutic effect are not particularly limited. The concomitant medicine can be used for any diseases, as long as it complements and/or enhances the preventive and/or therapeutic efficacy of the compound of the present invention.

The compound(s) of the present invention can be used with an existing chemotherapeutic concomitantly or in a mixture form. Examples of the chemotherapeutic include an alkylation agent, nitrosourea agent, antimetabolite, anticancer antibiotics, vegetable-origin alkaloid, topoisomerase inhibitor, hormone drug, hormone antagonist, aromatase inhibitor, P-glycoprotein inhibitor, platinum complex derivative, other immunotherapeutic drugs and other anticancer drugs. Further, it can be used with a cancer treatment adjunct, such as a leucopenia (neutropenia) treatment drug, thrombocytopenia treatment drug, antiemetic and cancer pain intervention drug, concomitantly or in a mixture form.

In one embodiment, the compound(s) of the present invention can be used with other immunomodulators and/or a potentiating agent concomitantly or in a mixture form. Examples of the immunomodulator include various cytokines, vaccines and adjuvants. Examples of these cytokines, vaccines and adjuvants that stimulates immune responses include but not limited to GM-CSF, M-CSF, G-CSF, interferon-α, β, or γ, IL-1, IL-2, IL-3, IL-12, Poly (I:C) and $C_pG$,.

In another embodiment, the potentiating agents includes cyclophosphamide and analogs of cyclophosphamide, anti-TGFβ and Imatinib (Gleevac), a mitosis inhibitor, such as paclitaxel, Sunitinib (Sutent) or other antiangiogenic agents, an aromatase inhibitor, such as letrozole, an A2a adenosine receptor (A2AR) antagonist, an angiogenesis inhibitor, anthracyclines, oxaliplatin, doxorubicin, TLR4 antagonists, and IL-18 antagonists.

Unless defined otherwise, all technical and scientific terms used herein have the same meaning as is commonly understood by one of skill in art to which the subject matter herein belongs. As used herein, the following definitions are supplied in order to facilitate the understanding of the present invention.

As used herein, the term 'compound(s)' refers to the compounds disclosed in the present invention.

As used herein, the term "comprise" or "comprising" is generally used in the sense of include, that is to say permitting the presence of one or more features or components.

As used herein, the term "including" as well as other forms, such as "include", "includes," and "included," is not limiting.

As used herein, the term "amino" refers to —$NH_2$ group. Unless set forth or recited to the contrary, all amino groups described or claimed herein may be substituted or unsubstituted.

As used herein, the term "amino acid" refers to amino acids having L or D stereochemistry at the alpha carbon.

"Pharmaceutically acceptable salt" is taken to mean an active ingredient, which comprises a compound of the formula (I) in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

The term "stereoisomer" refers to any enantiomers, diastereoisomers, or geometrical isomers of the compounds of formula (I), wherever they are chiral or when they bear one or more double bond. When the compounds of the formula (I) and related formulae are chiral, they can exist in racemic or in optically active form. Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis. In the case of racemic amines, diastereomers are formed from the mixture by reaction with an optically active resolving agent. Examples of suitable resolving agents are optically active acids such as the R and S forms of tartaric acid, diacetyltartaric acid, dibenzoyltartaric acid, mandelic acid, malic acid, lactic acid, suitable N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel).

The term "subject" includes mammals (especially humans) and other animals, such as domestic animals (e.g., household pets including cats and dogs) and non-domestic animals (such as wildlife).

"Therapeutically effective amount" or "efficient amount" refers to sufficient amount of the compound(s) of the present invention that (i) treats or prevents the particular disease, disorder or syndrome (ii) attenuates, ameliorates or eliminates one or more symptoms of the particular disease, disorder or syndrome or (iii) prevents or delays the onset of one or more symptoms of the particular disease, disorder or syndrome described herein. In the case of cancer, the therapeutically effective amount of the drug may decrease the number of cancer cells; decrease the cancer size; inhibit (i.e., slow to some extent and alternatively stop) cancer cell infiltration into peripheral organs; suppress (i.e., slow to some extent and alternatively stop) tumor metastasis; inhibit, to some extent, tumor growth; and/or relieve to some extent one or more of the symptoms associated with the cancer. In the case of infectious disease states, the therapeutic effective amount is an amount sufficient to decrease or alleviate an infectious diseases, the symptoms of an infections caused by bacterial, viral and fungal.

Naturally-occurring amino acids are identified throughout by the conventional three-letter abbreviations indicated in the below Table 2.

TABLE 2

(Amino acid codes)

| Name | 3-letter code |
| --- | --- |
| Asparagine | Asn |
| Aspartic acid | Asp |
| Alanine | Ala |
| Glutamic acid | Glu |
| Glutamine | Gln |
| Phenylalanin | Phe |
| Serine | Ser |
| Threonine | Thr |

The abbreviations used in the entire specification may be summarized hereinbelow with their particular meaning.

° C. (degree Celsius); δ (delta); % (percentage); brine (NaCl solution); $CH_2Cl_2$/DCM (Dichloromethane); br s (Broad singlet); $Cs_2CO_3$ (Caesium carbonate); d (Doublet); DMF (Dimethyl formamide); DMSO (Dimethyl sulphoxide); DMSO-$d_6$ (Deuterated DMSO); EDC.HCl/EDCI (1-(3-Dimethyl aminopropyl)-3-carbodiimide hydrochloride); $Et_2NH$ (Diethylamine); Fmoc (Fluorenylmethyloxycarbonyl chloride); g or gr (gram); H or $H_2$ (Hydrogen); $H_2O$ (Water); HOBt/HOBT (1-Hydroxy benzotriazole); HCl (Hydrochloric acid); h or hr (Hours); Hz (Hertz); HPLC (High-performance liquid chromatography); $I_2$ (Iodine); $K_2CO_3$ (Potassium carbonate); LCMS (Liquid chromatography mass spectroscopy); MeOH (Methanol); mmol (Millimoles); M (Molar); μl (Microliter); mL (Milliliter); mg (Milligram); m (Multiplet); MHz (Megahertz); MS (ES) (Mass spectroscopy-electro spray); min. (Minutes); Na (Sodium); $NaHCO_3$ (Sodium bicarbonate); $NH_2NH_2.H_2O$ (Hydrazine hydrate); NMM (N-methyl morpholine); $Na_2SO_4$ (Sodium sulphate); $N_2$ (Nitrogen); NMR (Nuclear magnetic resonance spectroscopy); PD-L1 (Programmed death-ligand 1); PD-L2 (Programmed cell death 1 ligand 2); prep-HPLC/preparative HPLC (Preparative High-performance liquid chromatography); S (Singlet); $^tBu$ (tertiary butyl); TEA/$Et_3N$ (Triethyl amine); TLC (Thin Layer Chromatography); THF (Tetrahydrofuran); TIPS (Triisopropylsilane); TFA/$CF_3COOH$ (Trifluoroacetic acid); t (Triplet); $t_R$=(Retention time); TPP (Triphenylphosphine); etc.

EXPERIMENTAL

An embodiment of the present invention provides the preparation of compounds of formula (I) according to the procedures of the following examples, using appropriate materials. Those skilled in the art will understand that known variations of the conditions and processes of the following preparative procedures can be used to prepare these compounds. Moreover, by utilizing the procedures described in detail, one of ordinary skill in the art can prepare additional compounds of the present invention.

The starting materials are generally available from commercial sources such as Sigma-Aldrich, USA or Germany; Chem-Impex USA; G.L. Biochem, China and Spectrochem, India.

Purification and Characterization of Compounds

Analytical HPLC method: Analytical HPLC was performed using on ZIC HILIC 200 A° column (4.6 mm×250 mm, 5 μm), Flow rate: 1.0 mL/min. The elution conditions used are: Buffer A: 5 mmol ammonium acetate, Buffer B: Acetonitrile, Equilibration of the column with 90% buffer B and elution by a gradient of 90% to 40% buffer B during 30 min.

Preparative HPLC Method: Preparative HPLC was performed using on SeQuant ZIC HILIC 200 A° column (10 mm×250 mm, 5 μm), Flow rate: 5.0 ml/min. The elution conditions used are: Buffer A: 5 mmol ammonium acetate (adjust to pH-4 with Acetic Acid), Buffer B: Acetonitrile, Equilibration of the column with 90% buffer B and elution by a gradient of 90% to 40% buffer B during 20 min.

LCMS was performed on AP1 2000 LC/MS/MS triple quad (Applied bio systems) with Agilent 1100 series HPLC with G1315 B DAD, using Mercury MS column or using Agilent LC/MSD VL single quad with Agilent 1100 series HPLC with G1315 B DAD, using Mercury MS column or using Shimadzu LCMS 2020 single quad with Prominence UFLC system with SPD-20 A DAD.

Example 1

Synthesis of Compound 1

Step 1a:

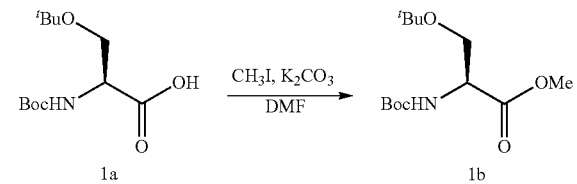

Potassium carbonate (7.9 g, 57.39 mmol) and Methyl iodide (1.3 mL, 21.04 mmol) were added to a solution of compound 1a (5.0 g, 19.13 mmol) in DMF (35 mL) and stirred at room temperature for 2 h. The completeness of the reaction was confirmed by TLC analysis. The reaction mixture was partitioned between water and ethyl acetate. Organic layer was washed with water, brine, dried over Na₂SO₄ and evaporated under reduced pressure to get 5.0 g of compound 1 b (Yield: 96.1%). LCMS: 176.1 (M-Boc)⁺.

Step 1b:

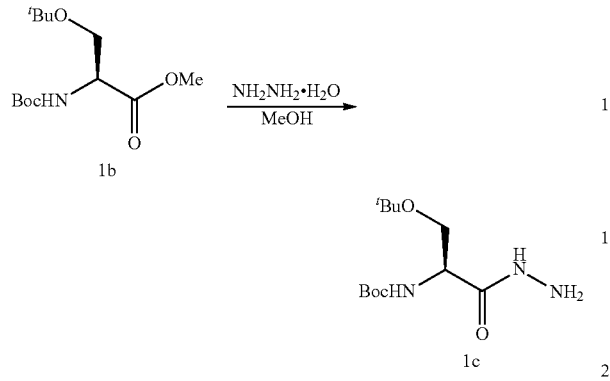

Hydrazine hydrate (7.2 mL) was added to a solution of compound 1b (5.0 g, 18.16 mmol) in methanol (30 mL) and stirred at room temperature for 2 h. The completeness of the reaction was confirmed by TLC analysis. The reaction mixture was evaporated under reduced pressure, the residue obtained was partitioned between water and ethyl acetate. Organic layer was washed with water, brine, dried over Na₂SO₄ and evaporated under reduced pressure to get 4.0 g of compound 1c (Yield: 80.0%). LCMS: 276.3 (M+H)⁺.

Step 1c:

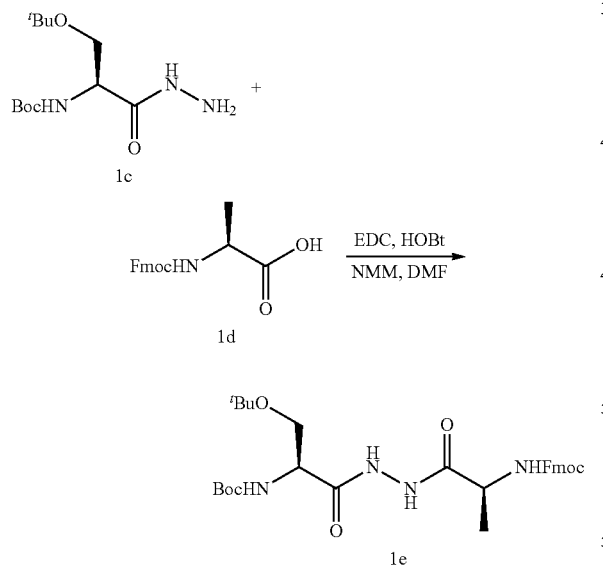

NMM (0.67 ml, 6.52 mmol) was slowly added to a stirred solution of 1c (1.2 g, 4.35 mmol), 1d (1.43 g, 4.35 mmol), HOBt (0.7 g, 5.22 mmol) and EDC.HCl (0.99 g, 5.22 mmol) in DMF (15 mL) at 0°. The reaction mixture was stirred at room temperature for 12 h. The completeness of the reaction was confirmed by TLC analysis. The reaction was quenched with ice and the solid precipitated was filtered and dried under vacuum to obtain 2.0 g of pure product 1e (Yield: 83.3%). LCMS: 591.5 (M+Na)⁺.

Step 1d:

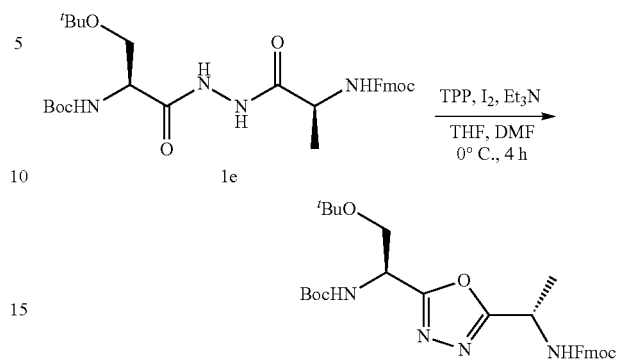

To a stirred solution of 1e (1.5 g, 2.63 mmol) in dry THF (15.0 mL) and DMF (5.0 mL) triphenylphosphine (1.38 g, 5.27 mmol) and iodine (1.33 g, 5.27 mmol) were added at 0° C. After the iodine was completely dissolved, Et₃N (1.52 mL, 10.54 mmol) was added to this reaction mixture at ice cold temperature. Reaction mixture was allowed to attain room temperature and stirred for 4 h. The completeness of the reaction was confirmed by TLC analysis. The reaction was quenched with ice water and extracted with ethyl acetate. Organic layer was washed with saturated sodium thiosulphate and brine solution. The separated Organic layer was dried over Na₂SO₄ and evaporated under reduced pressure to get residue, which was further purified by silica gel column chromatography (eluent: 30% ethyl acetate in hexane) to afford 0.8 g of compound 1f (Yield: 55%). LCMS: 551.3 (M+H)⁺.

Step 1e:

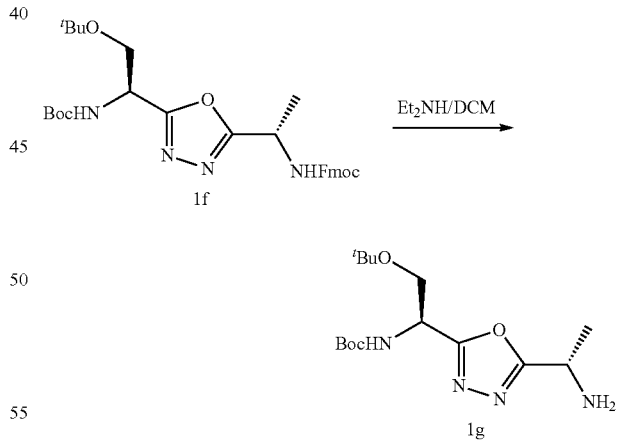

Fmoc group was deprotected by the addition of diethylamine (20.0 mL) to a solution of compound 1f (0.8 g, 1.45 mmol) in CH₂Cl₂ (20.0 mL) at 0° C. The reaction was stirred at room temperature for 2 h. The resulting solution was concentrated in vacuum to get a thick gummy residue. The crude compound was purified by neutral alumina column chromatography (eluent: 2% methanol in chloroform) to afford 0.38 g of compound 1g (Yield: 80.0%): LCMS: 329.4 (M+H)⁺.

Step 1f:

Synthesis of Compound 1h (NO$_2$—C$_6$H$_4$—OCO-Thr(tBu)-O$^t$Bu)

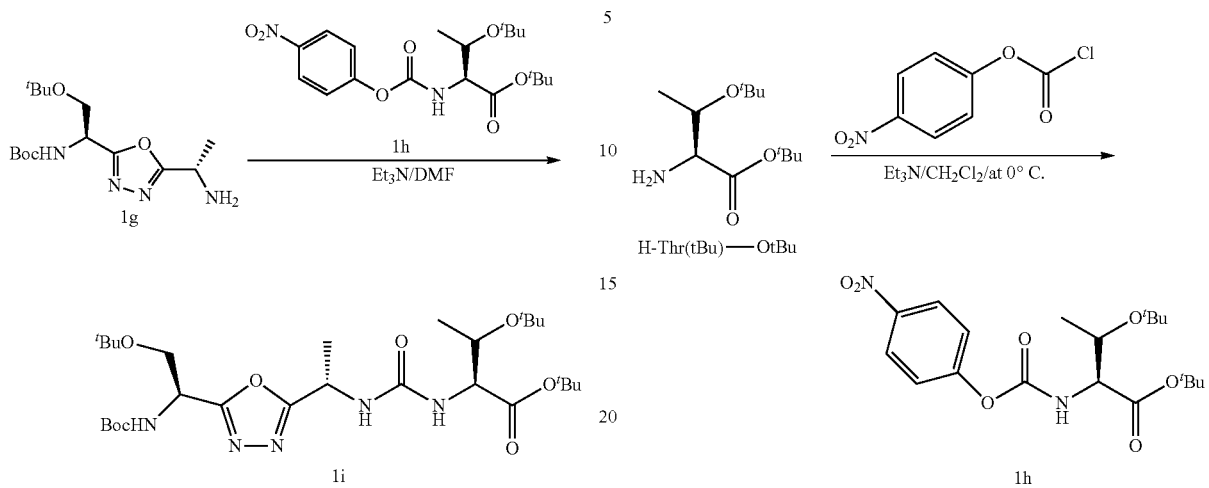

Compound 1g (0.38 g, 1.16 mmol), TEA (0.33 mL, 2.32 mmol) dissolved in DMF (10 mL) were added drop wise to a solution of 1h (0.55 g, 1.39 mmol) at 0° for urea bond formation and the mixture was stirred at room temperature for 2 h. The completeness of the reaction was confirmed by TLC analysis. The reaction was quenched with ice water, the solid precipitated was filtered and dried under vacuum to get crude compound, which was further purified by silica gel column chromatography (eluent: 0-35% ethyl acetate in hexane) to get 0.4 g of product 1i (Yield: 59.7%). LCMS: 586.4 (M+H)$^+$.

Step 1g:

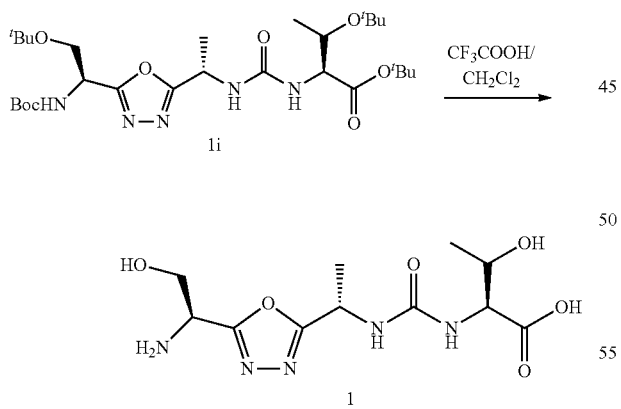

To a solution of compound 1i (0.4 g, 0.68 mmol) in CH$_2$Cl$_2$ (5 m L), trifluoroacetic acid (5 mL) and catalytic amount of triisopropylsilane were added and stirred at room temperature for 3 h to remove the acid sensitive protecting groups. The resulting solution was concentrated under nitrogen and the solid material was purified by preparative HPLC method as described under experimental conditions (Yield: 0.05 g). LCMS: 318.0 (M+H)$^+$; HPLC: $t_R$=10.96 min.

To a solution of 4-nitrophenylchloroformate (4.79 g, 23.77 mmol) in DCM (25.0 mL) was added a solution of H-Thr(tBu)-OtBu (5.0 g, 21.61 mmol) TEA (6.2 mL, 43.22 mmol) in CH$_2$Cl$_2$ (25 mL) slowly at 0° C. and allowed to stir for 30 min. The completion of the reaction was confirmed by TLC analysis. After completion of reaction it was diluted with DCM and washed with 1.0 M of citric acid followed by 1.0 M sodium carbonate solution. The organic layer was dried over Na$_2$SO$_4$ and evaporated under reduced pressure to afford crude compound 1h, which was further purified by silica gel column chromatography (eluent: 0-5% ethyl acetate in hexane) to get 3.0 g of product 1h. $^1$H NMR (CDCl$_3$, 400 MHz): δ 1.17 (s, 9H), 1.28 (d, 3H), 1.50 (s, 9H), 4.11 (m, 1H), 4.28 (m, 1H), 5.89 (d, 1H), 7.37 (d, 2H), 8.26 (d, 2H).

Example 2

Synthesis of Compound 2

Step 2a:

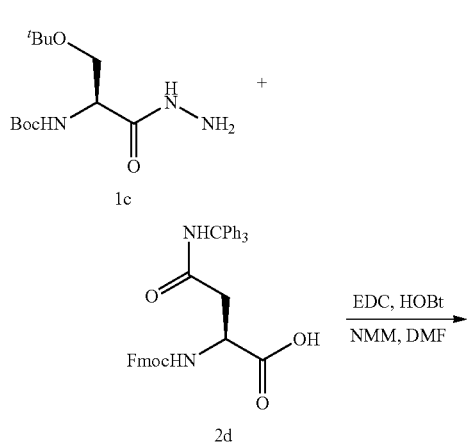

-continued

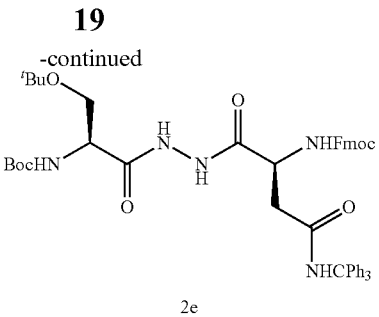

2e

NMM (1.8 mL, 18.15 mmol) was slowly added to a stirred solution of 1c (2.0 g, 7.26 mmol), 2d (4.3 g, 7.26 mmol), HOBt (1.17 g, 8.7 mmol) and EDC.HCl (1.66 g, 8.7 mmol) in DMF (15 mL) at 0°. The reaction mixture was stirred at room temperature for 12 h. The completeness of the reaction was confirmed by TLC analysis. The reaction was quenched with ice, the solid precipitated was filtered and dried under vacuum to afford 3.7 g of pure product 2e (Yield: 59.6%). LCMS: 854.4 (M+H)⁺.

Step 2b:

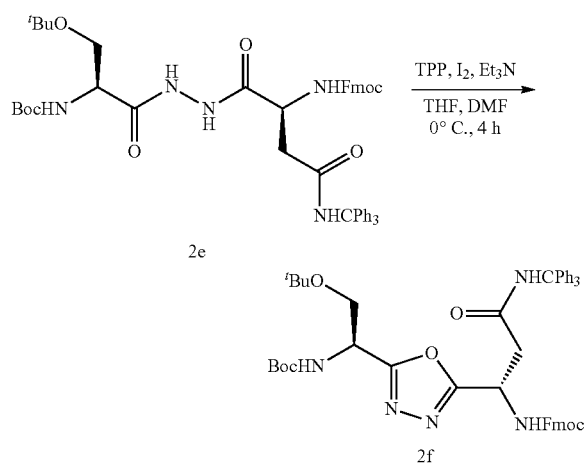

To a stirred solution of 2e (3.7 g, 4.33 mmol) dissolved in dry THF (25.0 mL) and DMF (10.0 mL), triphenylphosphine (2.28 g, 8.66 mmol) and iodine (2.2 g, 8.66 mmol) were added at 0. After the iodine was completely dissolved, Et₃N (2.5 mL, 17.32 mmol) was added at same temperature. The reaction mixture was stirred at room temperature for 4 h. The completeness of the reaction was confirmed by TLC analysis. The reaction was quenched with ice water and extracted with ethyl acetate. The organic layer was washed with saturated sodium thiosulphate and brine solution. The separated organic layer was dried over Na₂SO₄ and evaporated under reduced pressure, which was further purified by silica gel column chromatography (eluent: 30% ethyl acetate in hexane) to get 2.0 g of compound 2f (Yield: 55%). LCMS: 858.4 (M+Na)⁺.

Step 2c:

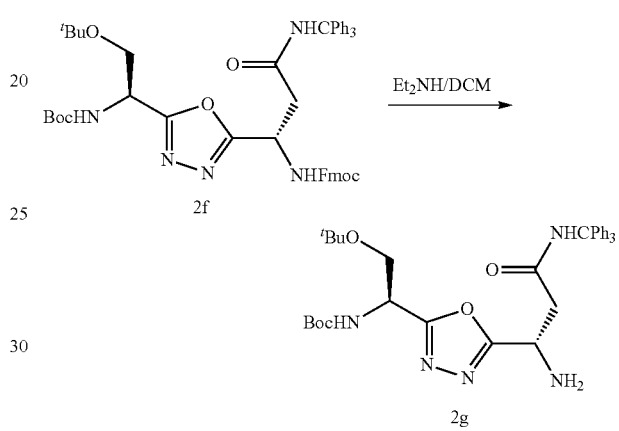

Diethylamine (30.0 mL) was added to a solution of compound 2f (2.0 g, 1.17 mmol) in CH₂Cl₂ (30.0 mL) at 0°. The reaction mixture was stirred at room temperature for 1 h. The resulting solution was concentrated in vacuum to get a thick gummy residue. The crude compound was purified by neutral alumina column chromatography (eluent: 2% methanol in chloroform) to afford 1.0 g of compound 2g (Yield: 71.4%). LCMS: 614.5 (M+H)⁺.

Step 2d:

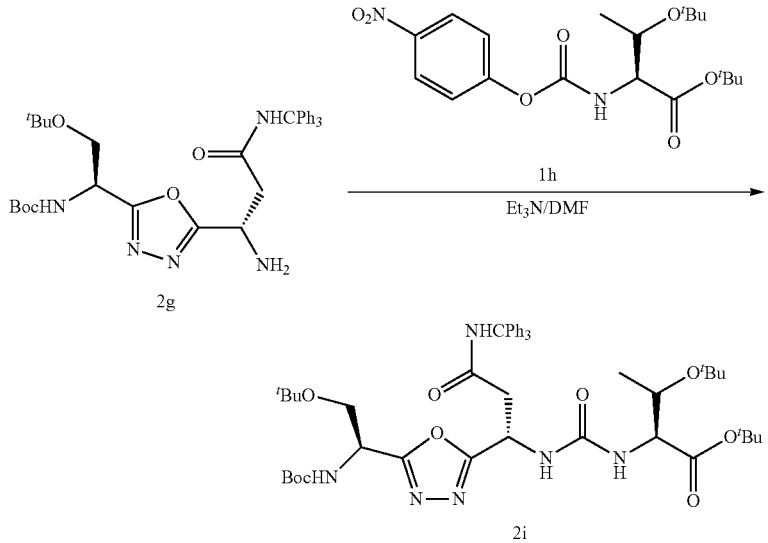

Compound 2g (1.0 g, 1.63 mmol) and TEA (0.47 mL, 3.2 mmol) dissolved in DMF (10 m L) were added drop wise to a solution of 1h (0.7 g, 1.79 mmol) at 0. The reaction mixture was then allowed to reach room temperature and continued the stirring for 2 h. The completeness of the reaction was confirmed by TLC analysis. The reaction was quenched with ice water, the solid precipitated was filtered and dried under vacuum. The crude compound obtained was further purified by silica gel column chromatography (eluent: 0-30% ethyl acetate in hexane) to get 0.8 g of product 2i (Yield: 57.1%). LCMS: 871.6 (M+H)$^+$.

Step 2e:

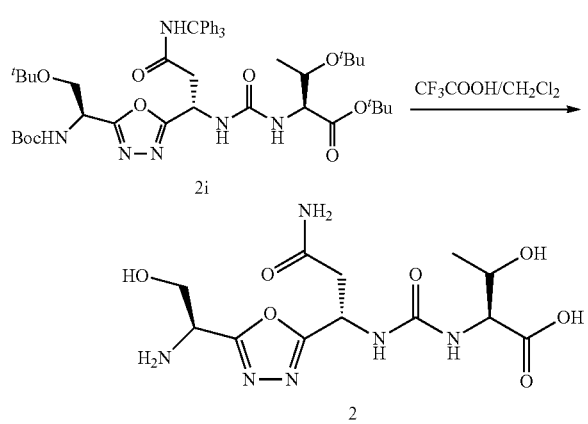

To a solution of compound 2i (0.8 g, 0.92 mmol) in CH$_2$Cl$_2$ (6 m L), trifluoroacetic acid (6 mL) and catalytic amount of triisopropylsilane were added and stirred at room temperature for 3 h. The resulting solution was concentrated under nitrogen and the solid material was purified by preparative HPLC method described under experimental conditions (Yield: 0.065 g). HPLC: $t_R$=12.01 min.; LCMS: 361.34 (M+H)$^+$.

Example 3

Synthesis of Compound 3

Step 3a:

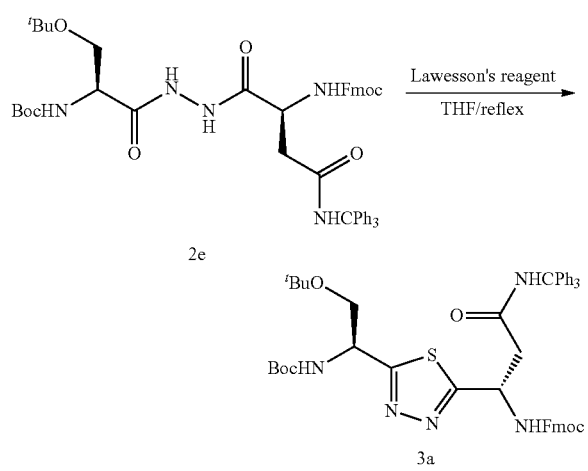

Lawesson's reagent (2.85 g, 7.03 mmol) was added to a solution of compound 2e (4 g, 4.68 mmol) in THF (40 mL) and stirred at 75° C. for 4 h. The completeness of the reaction was confirmed by TLC analysis. The reaction mixture was evaporated under reduced pressure and the obtained residue was partitioned between ice water and ethyl acetate. The organic layer was washed with NaHCO$_3$ solution followed brine solution. The organic layer was dried over Na$_2$SO$_4$, filtered and evaporated under reduced pressure to get residue which was further purified by silica gel column chromatography (eluent: 0-5% ethyl acetate in hexane) to afford 2.7 g of compound 3a (Yield: 67.66%). LCMS: 852.3 (M+H)$^+$.

Step 3b:

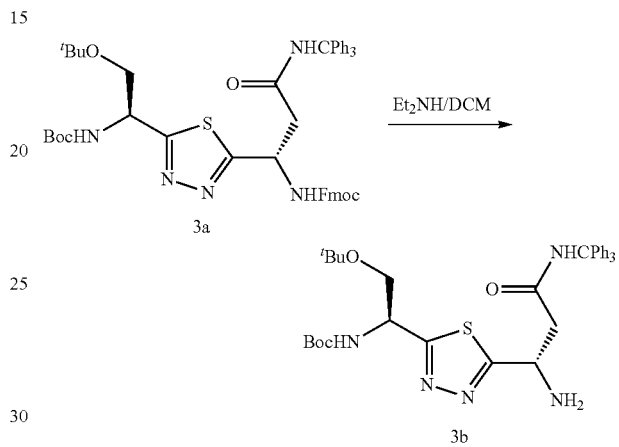

Fmoc group on compound 3a was deprotected by adding diethylamine (3.8 mL) to the solution of compound 3a (1 g, 1.17 mmol) in CH$_2$Cl$_2$ (3.8 mL). The reaction mixture was stirred at room temperature for 30 min. The resulting solution was concentrated in vacuum to get a thick gummy residue. The crude compound was purified by neutral alumina column chromatography (eluent: 0-50% ethyl acetate in hexane then 0-5% methanol in chloroform) to attain 0.62 g of compound 3b. LCMS: 630.5 (M+H)$^+$.

Step 3c:

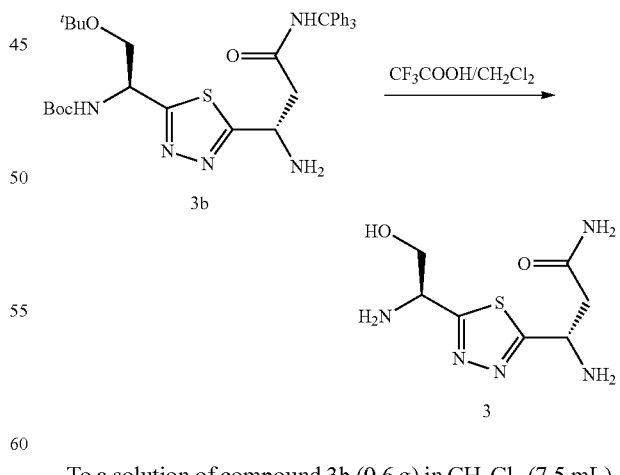

To a solution of compound 3b (0.6 g) in CH$_2$Cl$_2$ (7.5 mL), trifluoroacetic acid (2.5 mL) and catalytic amount of triisopropylsilane were added and stirred at room temperature for 3 h. The resulting solution was concentrated in vacuum to get 0.13 g of compound 3 which was purified by preparative HPLC method described under experimental conditions. LCMS: 232.3 (M+H)$^+$.

Example 4

Synthesis of Compound 4

Step 4a:

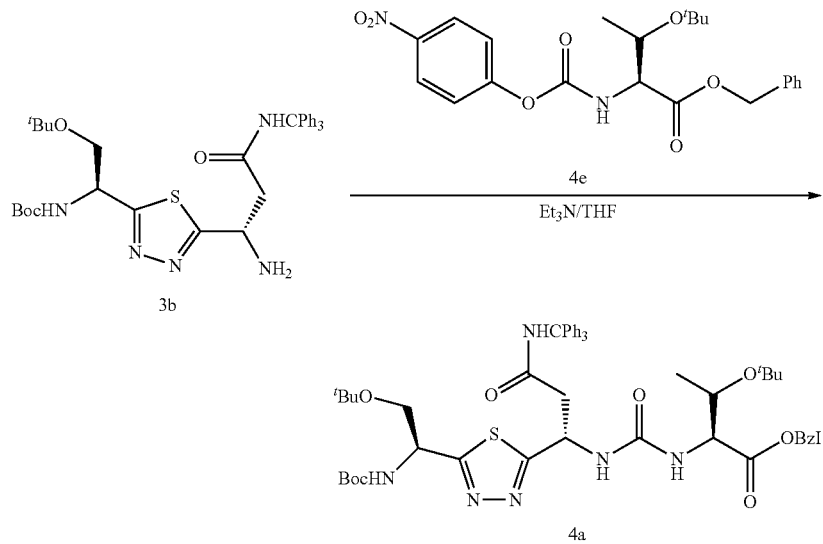

The urea linkage was carried out by coupling of compound 3b (0.5 g, 7.9 mmol) in THF (10 m L) at room temperature with compound 4e (0.34 g, 7.9 mmol). The coupling was initiated by the addition of TEA (0.16 g, 15.8 mmol) in THF (10 m L) and the resultant mixture was stirred at room temperature. After 12 h, THF was evaporated from the reaction mass, and partitioned between water and ethyl acetate. The organic layer was washed with water, brine, dried over $Na_2SO_4$ and evaporated under reduced pressure to yield 4a, which was further purified by silica gel column chromatography (eluent: 0-50% ethyl acetate in hexane) to get 0.45 g of product 4a (Yield: 61.64%). LCMS: 921.8 $(M+H)^+$.

Step 4b:

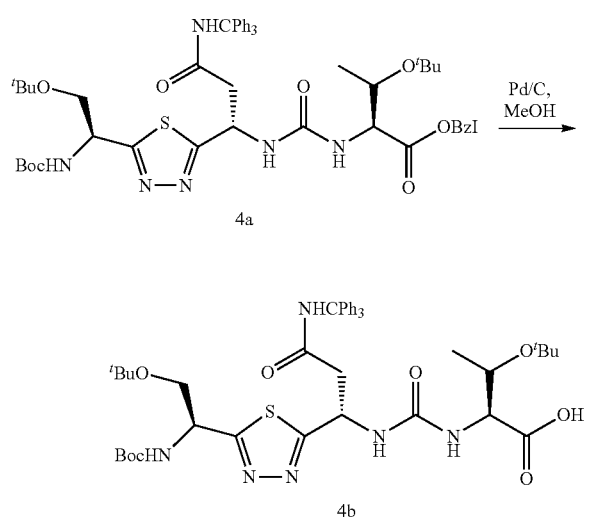

To a solution of compound 4a (0.55 g) in methanol (20 mL), was added 10% Pd—C (0.15 g) under inert atmosphere. The mixture was stirred for 1 h under $H_2$ atmosphere. The completion of the reaction was confirmed by TLC analysis. The Pd—C catalyst was then removed by filtration through a Celite® pad and washed with 20 mL of methanol. The combined organic filtrate on evaporation under reduced pressure resulted in the isolation of the product 4b (Yield: 0.42 g, 85.71%). LCMS: 831.5 $(M+H)^+$.

Step 4c:

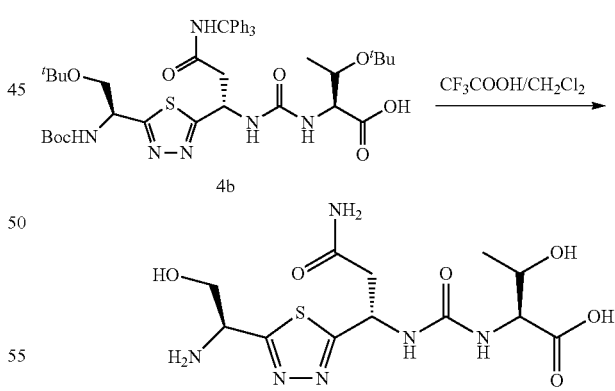

To a solution of compound 4b (0.2 g, 0.3 mmol) in $CH_2Cl_2$ (5 mL), trifluoroacetic acid (5 mL) and catalytic amount of triisopropylsilane were added and stirred at room temperature for 3 h. The resulting solution was concentrated in vacuum and the solid material was purified by preparative HPLC method described under experimental conditions (Yield: 0.065 g). HPLC: $t_R$=14.1 min.; LCMS: 377.3 $(M+H)^+$.

Synthesis of Compound 4e, (NO₂—C₆H₄—OCO-Thr(OᵗBu)-Bzl,)

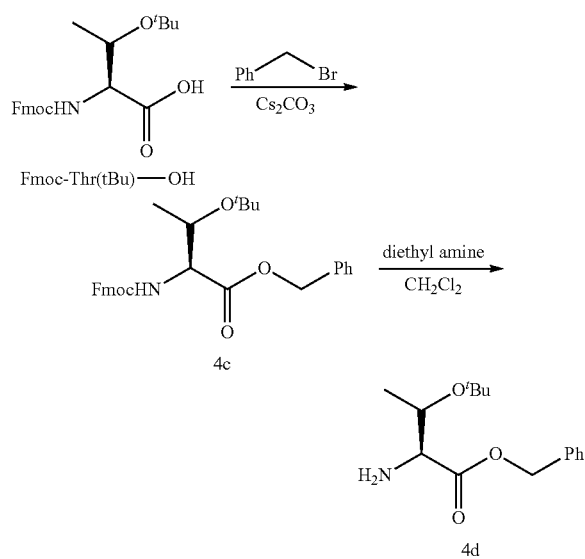

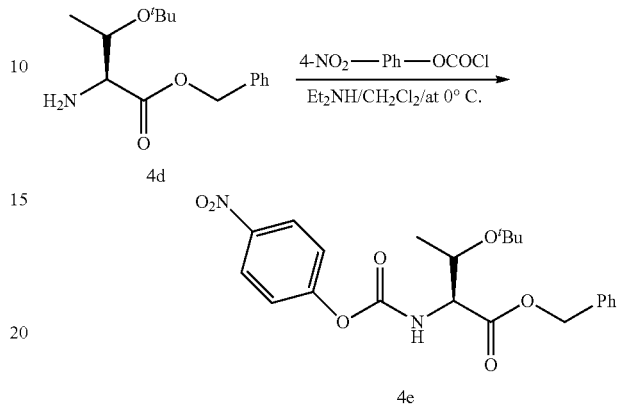

To a solution of compound Fmoc-Thr(ᵗBu)-OH (15 g, 37.73 mmol) in 100 mL of DMF, $Cs_2CO_3$ (14.75 g, 45.2 mmol) was added and the resulting mixture was cooled to 0. To the cooled reaction mixture benzyl bromide (7.74 g, 45.2 mmol) was added and the solution was stirred at ice cold temperature for 30 min and then at room temperature for 12 h. The reaction mixture was concentrated under reduced pressure and diluted with ethyl acetate. The organic layer was washed with water followed by brine solution and dried over $Na_2SO_4$. The filtered solution was concentrated and purified by silica gel column chromatogrophy (eluent: 0-30% ethyl acetate in hexane) to get 18 g of 4c as white solid. LCMS: 433.1 (M-OᵗBu)⁺, 397.2 (M-OBzl)⁺.

Fmoc group on compound 4c (25 g, 51.3 mmol) was deprotected by adding diethylamine (100 mL) to compound 4d (25 g, 51.3 mmol) in $CH_2Cl_2$ (100 mL) for 1 h with stirring at room temperature. The resulting solution was concentrated in vacuum and the thick residue was purified by neutral alumina column chromatography (eluent: 0-50% ethyl acetate in hexane then 0-5% methanol in chloroform) to afford 10.6 g of compound 4d. LCMS: 266.5 (M+H)⁺.

To a solution of compound 4d (1.5 g, 5.65 mmol) in $CH_2Cl_2$ (25 m L) was added TEA (1.14 g, 11.3 mmol) and the solution was stirred at room temperature for 5-10 min. To this mixture a solution of 4-nitrophenyl chloroformate (1.4 g, 6.78 mmol) in $CH_2Cl_2$ (10 mL) was added and the resultant mixture was stirred at room temperature for 12 h. The completion of the reaction was confirmed by TLC analysis. After completion of reaction it was diluted with DCM and washed with 1.0 M of sodium bisulphate solution followed by 1.0 M sodium carbonate solution. The organic layer was dried over $Na_2SO_4$, filtered and evaporated under reduced pressure to yield crude compound 4e, which was further purified by silica gel column chromatography (eluent: 0-20% ethyl acetate in hexane) to yield 0.7 g of product 4e. ¹H NMR (DMSO-d⁶, 300 MHz): δ 1.04 (s, 9H), 1.16 (d, 3H), 4.11 (m, 1H), 5.11 (m, 3H), 6.91 (d, 2H), 7.40 (m, 5H), 8.10 (d, 2H), 8.26 (br s, 1H).

The compounds in Table 3 below were prepared based on the experimental procedures described above.

TABLE 3

| Compound No. | Structure | LCMS (M + H)⁺ | HPLC $t_R$ in min |
|---|---|---|---|
| 5. | (structure) | 391.1 | 12.43 |
| 6. | (structure) | 377.1 | — |

TABLE 3-continued

| Compound No. | Structure | LCMS (M + H)+ | HPLC $t_R$ in min |
|---|---|---|---|
| 7. | 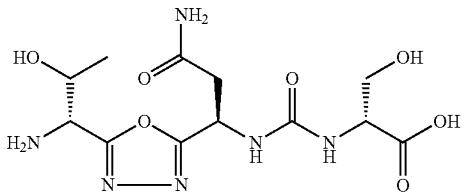 [SMILES: CC(O)[C@@H](N)c1nnc([C@@H](CC(N)=O)NC(=O)N[C@H](CO)C(=O)O)o1] | 361.1 | 12.21 |
| 8. | 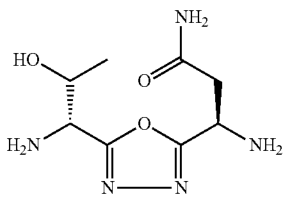 [SMILES: CC(O)[C@@H](N)c1nnc([C@H](N)CC(N)=O)o1] | 230.1 | 12.95 |
| 9. | 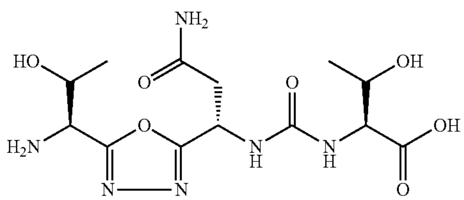 | 375.4 | 11.55 |
| 10. | 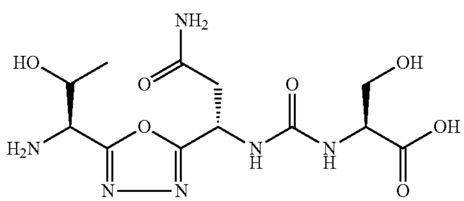 | 361.2 | 11.91 |
| 11. | 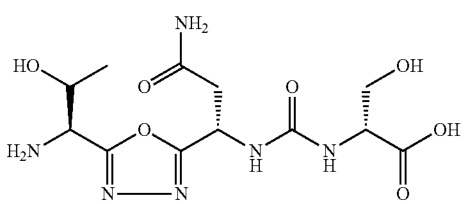 [SMILES: CC(O)[C@H](N)c1nnc([C@H](CC(N)=O)NC(=O)N[C@H](CO)C(=O)O)o1] | 361.1 | 12.08 |
| 12. | 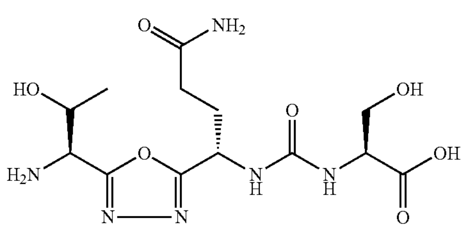 | 375.2 | 11.5 |
| 13. | 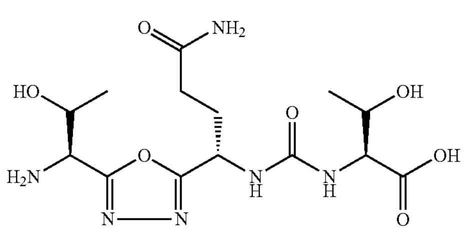 | 389.1 | 11.10 |

TABLE 3-continued

| Compound No. | Structure | LCMS (M + H)+ | HPLC $t_R$ in min |
|---|---|---|---|
| 14. | 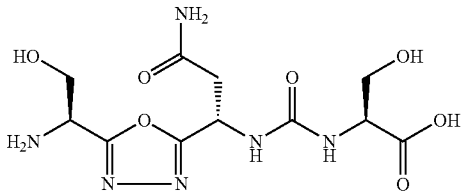 | 347.1 | 12.58 |
| 15. | 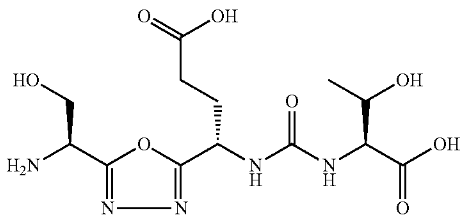 | 376.1 | 12.20 |
| 16. | 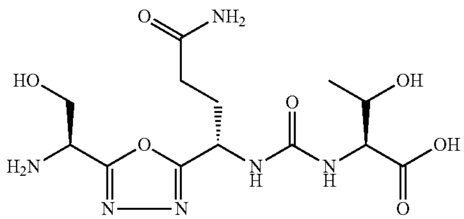 | 375.2 | 11.91 |
| 17. | 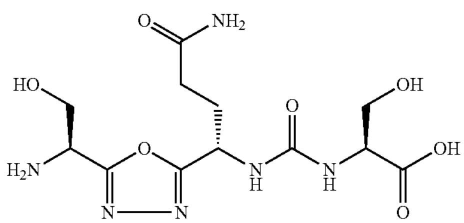 | 361.2 | 12.34 |
| 18. | 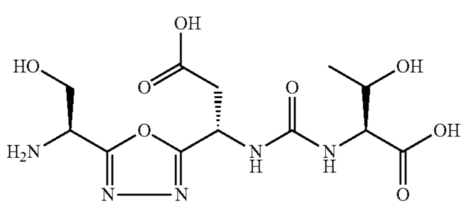 | 362.1 | 12.50 |
| 19. | 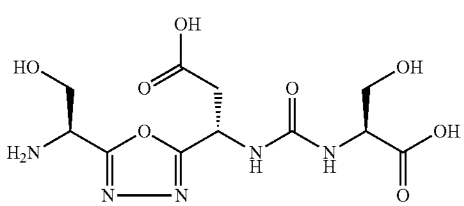 | 348.1 | 12.83 |
| 20. | 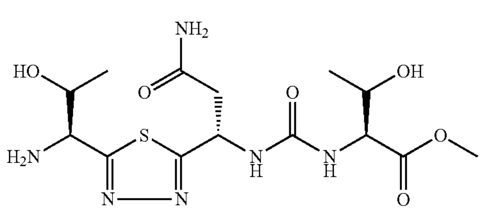 [SMILES: COC(=O)[C@@H](NC(=O)N[C@@H](CC(N)=O)c1nnc([C@@H](N)C(C)O)s1)C(C)O] | 391.1 | — |

The compounds shown in below Table 4, which can be prepared by following similar procedure as described above with suitable modification known to the one ordinary skilled in the art are also included in the scope of the present application.

TABLE 4

| Cmpd No. | Structure |
|---|---|
| 21. | (structure) |
| 22. | (structure) |
| 23. | (structure) |
| 24. | (structure) |
| 25. | (structure) |
| 26. | (structure) |
| 27. | (structure) |

TABLE 4-continued

| Cmpd No. | Structure |
|---|---|
| 28. | (structure) and |
| 29. | (structure) |

Rescue of Mouse Splenocyte Proliferation in the Presence of Recombinant PD-L1/PD-L2:

Recombinant mouse PD-L1 (rm-PDL-1, cat no: 1019-B7-100 and R&D Systems) were used as the source of PD-L1.

Requirement:

Mouse splenocytes harvested from 6-8 weeks old C57 BL6 mice; RPMI 1640 (GIBCO, Cat #11875); DMEM with high glucose (GIBCO, Cat # D6429); Fetal Bovine Serum [Hyclone, Cat # SH30071.03]; Penicillin (10000 unit/ml)—Streptomycin (10,000 μg/ml) Liquid (GIBCO, Cat #15140-122); MEM Sodium Pyruvate solution 100 mM (100×), Liquid (GIBCO, Cat #11360); Nonessential amino acid (GIBCO, Cat #11140); L-Glutamine (GIBCO, Cat #25030); Anti-CD3 antibody (eBiosciences—16-0032); Anti-CD28 antibody (eBiosciences—16-0281); ACK lysis buffer (1 mL) (GIBCO, Cat #-A10492); Histopaque (density-1.083 gm/mL) (SIGMA 10831); Trypan blue solution (SIGMA-T8154); 2 mL Norm Ject Luer Lock syringe-(Sigma 2014-12); 40 μM nylon cell strainer (BD FALCON 35230); Hemacytometer (Bright line—SIGMA Z359629); FACS Buffer (PBS/0.1% A BSA): Phosphate Buffered Saline (PBS) pH 7.2 (HiMedia TS1006) with 0.1% Bovine Serum Albumin (BSA) (SIGMA A7050) and sodium azide (SIGMA 08591); 5 mM stock solution of CFSE: CFSE stock solution was prepared by diluting lyophilized CFSE with 180 μL of Dimethyl sulfoxide (DMSO $C_2H_6SO$, SIGMA-D-5879) and aliquoted in to tubes for further use. Working concentrations were titrated from 10 μM to 1 μM. (eBioscience-650850-85); 0.05% Trypsin and 0.02% EDTA (SIGMA 59417C); 96-well format ELISA plates (Corning CLS3390); BD FACS caliber (E6016); Recombinant mouse B7-H1/PDL1 Fc Chimera, (rm-PD-L1 cat no: 1019-B7-100).

Protocol

Splenocyte Preparation and Culturing:

Splenocytes harvested in a 50 mL falcon tube by mashing mouse spleen in a 40 μm cell strainer were further treated with 1 mL ACK lysis buffer for 5 min at room temperature. After washing with 9 mL of RPMI complete media, cells were re-suspended in 3 mL of 1×PBS in a 15 mL tube. 3 mL of Histopaque was added carefully to the bottom of the tube without disturbing overlaying splenocyte suspension. After centrifuging at 800×g for 20 min at room temperature, the opaque layer of splenocytes was collected carefully without disturbing/mixing the layers. Splenocytes were washed twice with cold 1×PBS followed by total cell counting using Trypan Blue exclusion method and used further for cell based assays.

Splenocytes were cultured in RPMI complete media (RPMI+10% fetal bovine serum+1 mM sodium pyruvate+ 10,000 units/ml penicillin and 10,000 μg/ml streptomycin) and maintained in a $CO_2$ incubator with 5% $CO_2$ at 37° C.

CFSE Proliferation Assay:

CFSE is a dye that passively diffuses into cells and binds to intracellular proteins. $1 \times 10^6$ cells/mL of harvested splenocytes were treated with 5 μM of CFSE in pre-warmed 1×PBS/0.1% BSA solution for 10 min at 37° C. Excess CFSE was quenched using 5 volumes of ice-cold culture media to the cells and incubated on ice for 5 min. CFSE labelled splenocytes were further given three washes with ice cold complete RPMI media. CFSE labelled $1 \times 10^5$ splenocytes added to wells containing either MDA-MB231 cells ($1 \times 10^5$ cells cultured in high glucose DMEM medium) or recombinant human PDL-1 (100 ng/mL) and test compounds. Splenocytes were stimulated with anti-mouse CD3 and anti-mouse CD28 antibody (1 μg/mL each), and the culture was further incubated for 72 h at 37° C. with 5% $CO_2$. Cells were harvested and washed thrice with ice cold FACS buffer and % proliferation was analyzed by flow cytometry with 488 nm excitation and 521 nm emission filters.

Data Compilation, Processing and Inference:

Percent splenocyte proliferation was analyzed using cell quest FACS program and percent rescue of splenocyte proliferation by compound was estimated after deduction of % background proliferation value and normalising to % stimulated splenocyte proliferation (positive control) as 100%.

Stimulated splenocytes: Splenocytes+anti-CD3/CD28 stimulation

Background proliferation: Splenocytes+anti-CD3/CD28+ PD-L1

Compound proliferation: Splenocytes+anti-CD3/CD28+ PD-L1+Compound

Compound effect is examined by adding required concentration of compound to anti-CD3/CD28 stimulated splenocytes in presence of ligand (PDL-1).

TABLE 5

| Compound No. | Percent rescue of splenocyte proliferation (@100 nM compound concentration) |
|---|---|
| 1 | 61.2 |
| 2 | 80.3 |
| 3 | 48.4 |
| 4 | 60 |
| 9 | 74 |
| 10 | 58 |
| 12 | 92 |
| 13 | 75 |
| 14 | 53 |
| 15 | 69 |
| 16 | 56 |
| 17 | 53 |
| 18 | 68 |
| — | — |

What is claimed is:

1. A compound of formula (I)

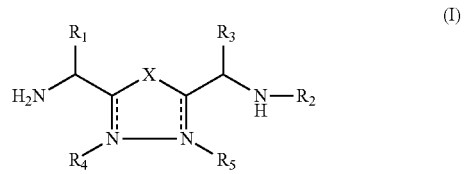

wherein,
$R_1$ represents —$CH_2OH$, —$CH(CH_3)OH$, —$CH_2Ph$, —$CH_3$, or —$CH_2C(O)NH_2$;
X is S or O;
$R_2$ is hydrogen or —CO-Aaa;
Aaa is an amino acid residue selected from Ser, Asn or Thr; wherein a C-terminus thereof is a free terminus, is amidated or is esterified;
$R_3$ represents —$CH_2OH$, —$CH_3$, —$CH_2CH_2C(O)OH$, —$CH_2CH_2C(O)NH_2$, —$CH_2C(O)NH_2$, or —$CH_2C(O)OH$;
--- is an optional bond; and
$R_4$ and $R_5$ independently are hydrogen or absent;
or a pharmaceutically acceptable salt or a stereoisomer thereof.

2. The compound of claim 1, having the structure of formula (IA):

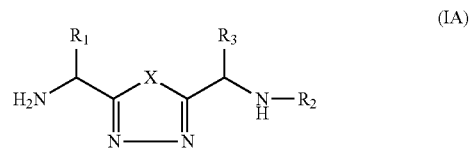

3. The compound of claim 2, wherein X is S.
4. The compound of claim 2, wherein X is O.
5. The compound of claim 2, wherein $R_2$ is hydrogen.
6. The compound of claim 1, having the structure of formula (IB):

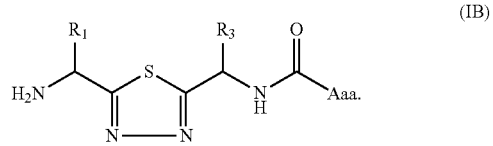

7. The compound of claim 6, wherein $R_1$ represents —$CH_2OH$ or —$CH(CH_3)OH$.
8. The compound of claim 6, wherein Aaa is an amino acid residue Ser or Thr; wherein the C-terminus is free.
9. The compound of claim 1, having the structure of formula (IC):

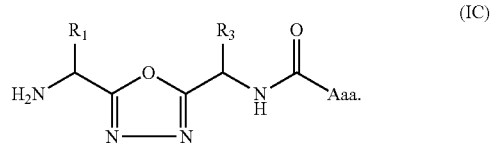

10. The compound of claim 9, wherein $R_1$ represents —$CH_2OH$ or —$CH(CH_3)OH$.

11. The compound of claim 9, wherein Aaa is an amino acid residue Ser or Thr; wherein the C-terminus is free.

12. The compound of claim 1, wherein X is S.

13. The compound of claim 12, wherein $R_2$ is —CO-Aaa.

14. The compound of claim 13, wherein Aaa is an amino acid residue Ser or Thr; wherein the C-terminus is free.

15. The compound of claim 1, wherein X is O.

16. The compound of claim 15, wherein $R_2$ is —CO-Aaa.

17. The compound of claim 16, wherein Aaa is an amino acid residue Ser or Thr; wherein the C-terminus is free.

18. The compound of claim 1, wherein $R_1$ represents —$CH_2OH$ or —$CH(CH_3)OH$.

19. The compound of claim 18, wherein $R_2$ is —CO-Aaa.

20. The compound of claim 19, wherein Aaa is an amino acid residue Ser or Thr; wherein the C-terminus is free.

21. The compound of claim 1, wherein $R_2$ is hydrogen.

22. The compound of claim 1, wherein $R_2$ is —CO-Aaa.

23. The compound of claim 22, wherein Aaa is an amino acid residue Ser or Thr; wherein the C-terminus is free.

24. The compound of claim 1, wherein $R_3$ represents —$CH_2CH_2C(O)OH$, —$CH_2CH_2C(O)NH_2$, —$CH_2C(O)NH_2$, or —$CH_2C(O)OH$.

25. The compound according to claim 1, or the pharmaceutically acceptable salt thereof, having the following structure:

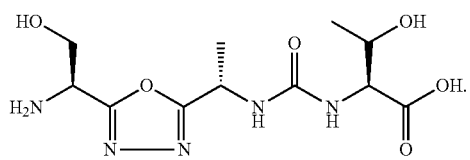 [SMILES: CC(O)[C@H](NC(=O)N[C@@H](C)c1nnc([C@@H](N)CO)o1)C(=O)O]

26. The compound according to claim 1, or the pharmaceutically acceptable salt thereof, having the following structure:

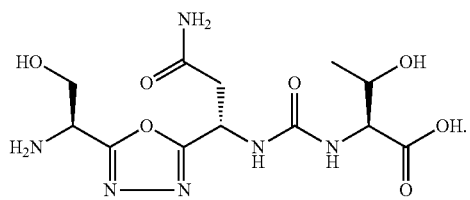

27. The compound according to claim 1, or the pharmaceutically acceptable salt thereof, having the following structure:

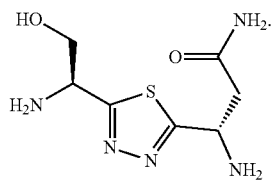

28. The compound according to claim 1, or the pharmaceutically acceptable salt thereof, having the following structure:

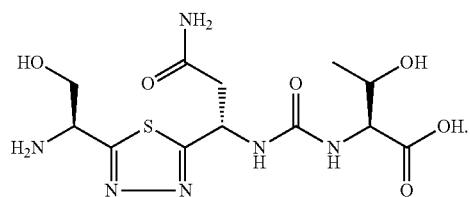 [SMILES: CC(O)[C@H](NC(=O)N[C@@H](CC(N)=O)c1nnc([C@@H](N)CO)s1)C(=O)O]

29. The compound according to claim 1, or the pharmaceutically acceptable salt thereof, having the following structure:

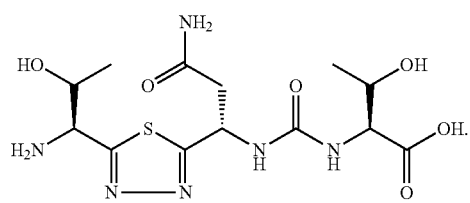 [SMILES: CC(O)[C@H](NC(=O)N[C@@H](CC(N)=O)c1nnc([C@@H](N)C(C)O)s1)C(=O)O]

30. The compound according to claim 1, or the pharmaceutically acceptable salt thereof, having the following structure:

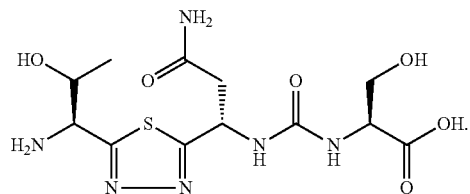 [SMILES: CC(O)[C@H](N)c1nnc([C@H](CC(N)=O)NC(=O)N[C@@H](CO)C(=O)O)s1]

31. The compound according to claim 1, or the pharmaceutically acceptable salt thereof, having the following structure:

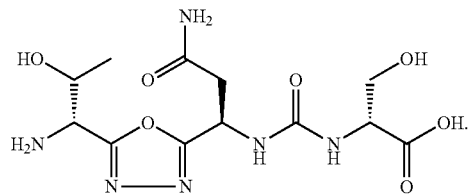 [SMILES: CC(O)[C@@H](N)c1nnc([C@@H](CC(N)=O)NC(=O)N[C@H](CO)C(=O)O)o1]

32. The compound according to claim 1, or the pharmaceutically acceptable salt thereof, having the following structure:

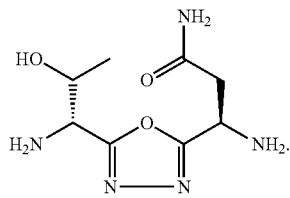 [SMILES: CC(O)[C@@H](N)c1nnc([C@H](N)CC(N)=O)o1]

33. The compound according to claim 1, or the pharmaceutically acceptable salt thereof, having the following structure:

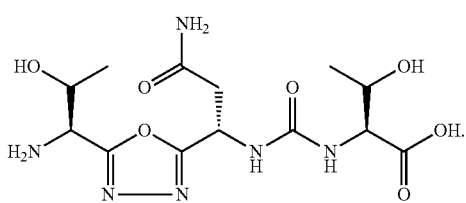 [SMILES: CC(O)[C@H](NC(=O)N[C@@H](CC(N)=O)c1nnc([C@@H](N)C(C)O)o1)C(=O)O]

34. The compound according to claim 1, or the pharmaceutically acceptable salt thereof, having the following structure:

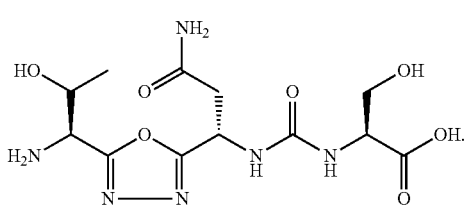 [SMILES: CC(O)[C@H](N)c1nnc([C@H](CC(N)=O)NC(=O)N[C@@H](CO)C(=O)O)o1]

35. The compound according to claim 1, or the pharmaceutically acceptable salt thereof, having the following structure:

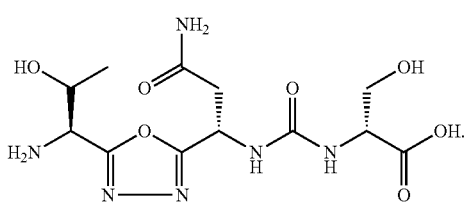 [SMILES: CC(O)[C@H](N)c1nnc([C@H](CC(N)=O)NC(=O)N[C@H](CO)C(=O)O)o1]

36. The compound according to claim 1, or the pharmaceutically acceptable salt thereof, having the following structure:

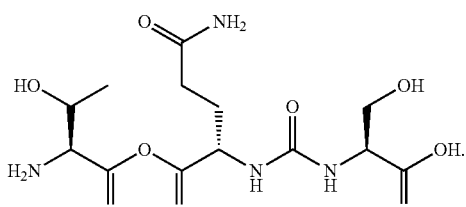

37. The compound according to claim 1, or the pharmaceutically acceptable salt thereof, having the following structure:

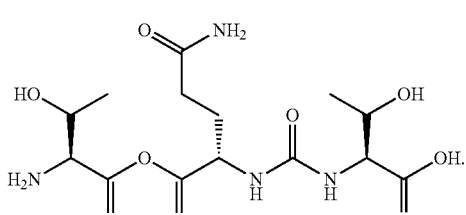

38. The compound according to claim 1, or the pharmaceutically acceptable salt thereof, having the following structure:

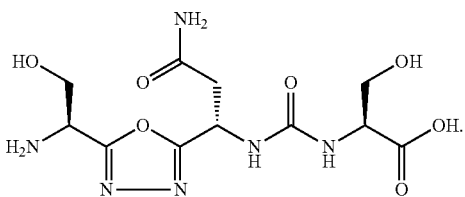 [SMILES: NC(=O)C[C@H](NC(=O)N[C@@H](CO)C(=O)O)c1nnc([C@@H](N)CO)o1]

39. The compound according to claim 1, or the pharmaceutically acceptable salt thereof, having the following structure:

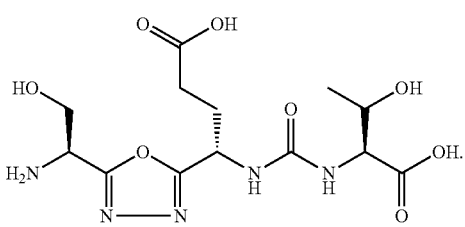

40. The compound according to claim 1, or the pharmaceutically acceptable salt thereof, having the following structure:

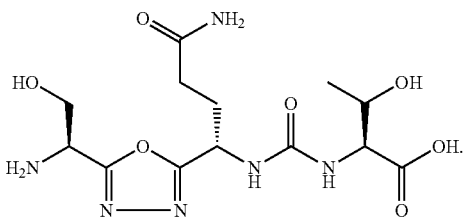 [SMILES: CC(O)[C@H](NC(=O)N[C@@H](CCC(N)=O)c1nnc([C@@H](N)CO)o1)C(=O)O]

41. The compound according to claim 1, or the pharmaceutically acceptable salt thereof, having the following structure:

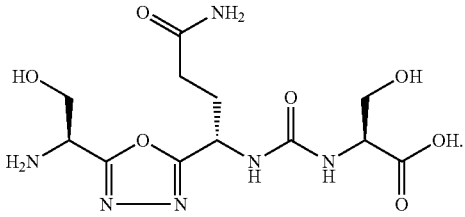 [SMILES: NC(=O)CC[C@H](NC(=O)N[C@@H](CO)C(=O)O)c1nnc([C@@H](N)CO)o1]

42. The compound according to claim 1, or the pharmaceutically acceptable salt thereof, having the following structure:

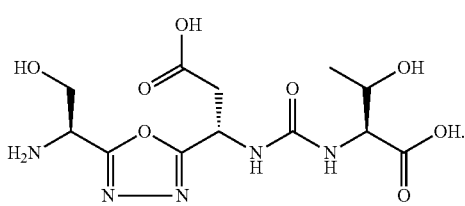 [SMILES: CC(O)[C@H](NC(=O)N[C@@H](CC(=O)O)c1nnc([C@@H](N)CO)o1)C(=O)O]

43. The compound according to claim 1, or the pharmaceutically acceptable salt thereof, having the following structure:

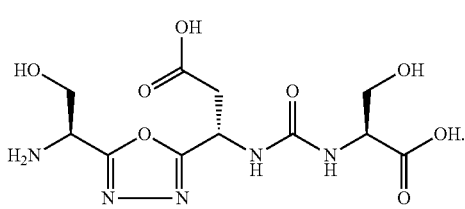

44. The compound according to claim 1, or the pharmaceutically acceptable salt thereof, having the following structure:

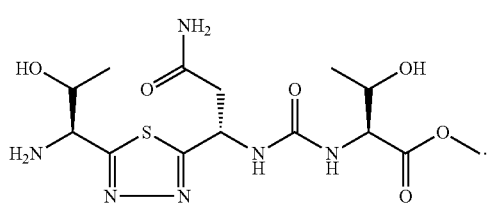 [SMILES: COC(=O)[C@@H](NC(=O)N[C@@H](CC(N)=O)c1nnc([C@@H](N)C(C)O)s1)C(C)O]

45. The compound according to claim 1, or the pharmaceutically acceptable salt thereof, having the following structure:

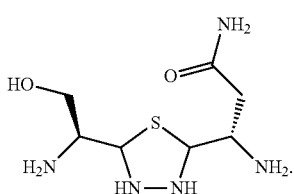 [SMILES: NC(=O)C[C@H](N)C1NNC([C@@H](N)CO)S1]

46. The compound according to claim 1, or the pharmaceutically acceptable salt thereof, having the following structure:

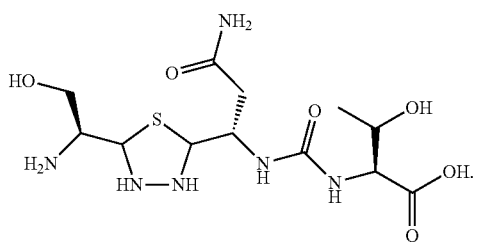

47. The compound according to claim 1, or the pharmaceutically acceptable salt thereof, having the following structure:

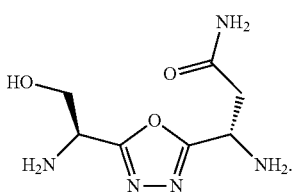 [SMILES: NC(=O)C[C@H](N)c1nnc([C@@H](N)CO)o1]

48. The compound according to claim 1, or the pharmaceutically acceptable salt thereof, having the following structure:

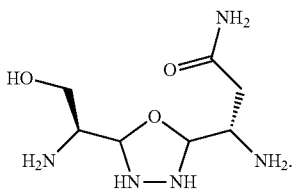 [SMILES: NC(=O)C[C@H](N)C1NNC([C@@H](N)CO)O1]

49. The compound according to claim 1, or the pharmaceutically acceptable salt thereof, having the following structure:

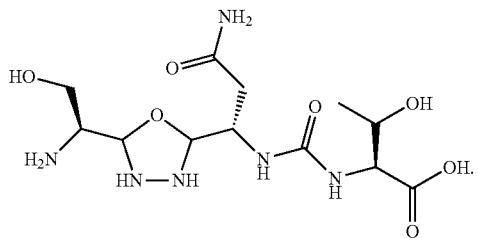 [SMILES: CC(O)[C@H](NC(=O)N[C@@H](CC(N)=O)C1NNC([C@@H](N)CO)O1)C(=O)O]

50. The compound according to claim 1, or the pharmaceutically acceptable salt thereof, having the following structure:

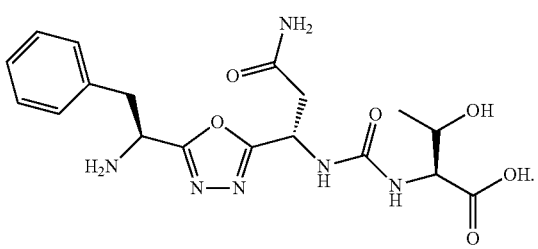 [SMILES: CC(O)[C@H](NC(=O)N[C@@H](CC(N)=O)c1nnc([C@@H](N)Cc2ccccc2)o1)C(=O)O]

51. The compound according to claim 1, or the pharmaceutically acceptable salt thereof, having the following structure:

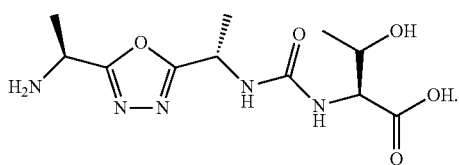 [SMILES: CC(O)[C@H](NC(=O)N[C@@H](C)c1nnc([C@H](C)N)o1)C(=O)O]

54. A pharmaceutical composition comprising a pharmaceutically acceptable carrier or excipient and at least one compound of formula (I) or a pharmaceutically acceptable salt or a stereoisomer thereof,

52. The compound according to claim 1, or the pharmaceutically acceptable salt thereof, having the following structure:

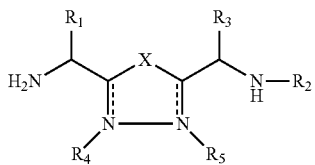

(I)

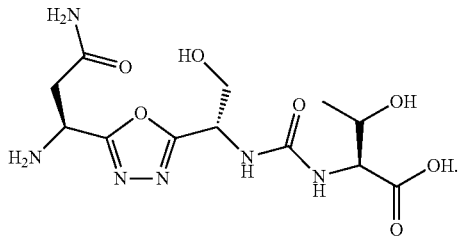

wherein,

R$_1$ represents —CH$_2$OH, —CH(CH$_3$)OH, —CH$_2$Ph, —CH$_3$, or —CH$_2$C(O)NH$_2$;

X is S or O;

R$_2$ is hydrogen or —CO-Aaa;

Aaa is an amino acid residue selected from Ser, Asn or Thr; wherein a C-terminus thereof is a free terminus, is amidated or is esterified;

53. The compound according to claim 1, or the pharmaceutically acceptable salt thereof, having the following structure:

R$_3$ represents —CH$_2$OH, —CH$_3$, —CH$_2$CH$_2$C(O)OH, —CH$_2$—CH$_2$C(O)NH$_2$, —CH$_2$C(O)NH$_2$, or —CH$_2$C(O)OH;

---is an optional bond; and

R$_4$ and R$_5$ independently are hydrogen or absent.

55. The pharmaceutical composition according to claim 54 further comprising at least one of an anticancer agent, a chemotherapy agent, or an antiproliferative compound.

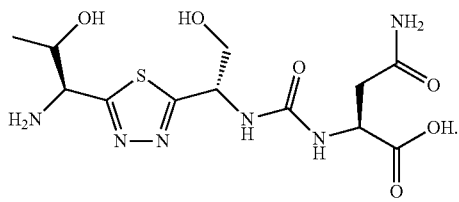 [SMILES: CC(O)[C@H](N)c1nnc([C@H](CO)NC(=O)N[C@@H](CC(N)=O)C(=O)O)s1]

* * * * *